(12) United States Patent
Clavelle et al.

(10) Patent No.: US 12,064,265 B2
(45) Date of Patent: Aug. 20, 2024

(54) SENSOR WINDOW WITH INTEGRATED ISOLATION FEATURE

(71) Applicant: APPLE INC., Cupertino, CA (US)

(72) Inventors: Adam T. Clavelle, San Francisco, CA (US); Maegan K. Spencer, Emerald Hills, CA (US); Jaden Alyssa Barney, Venetia, PA (US); Dale N. Memering, San Francisco, CA (US); Ueyn L. Block, Menlo Park, CA (US); Paul D. Mannheimer, Los Altos, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 17/881,917

(22) Filed: Aug. 5, 2022

(65) Prior Publication Data

US 2023/0022354 A1 Jan. 26, 2023

Related U.S. Application Data

(63) Continuation of application No. 16/900,045, filed on Jun. 12, 2020, now Pat. No. 11,406,325, which is a continuation of application No. 15/650,744, filed on Jul. 14, 2017, now Pat. No. 10,702,211.

(60) Provisional application No. 62/363,134, filed on Jul. 15, 2016.

(51) Int. Cl.
*A61B 5/00* (2006.01)
*A61B 5/024* (2006.01)
*A61B 5/1455* (2006.01)

(52) U.S. Cl.
CPC ........ *A61B 5/6824* (2013.01); *A61B 5/02422* (2013.01); *A61B 5/14552* (2013.01); *A61B 5/681* (2013.01); *A61B 5/6838* (2013.01); *A61B 2562/02* (2013.01); *A61B 2562/146* (2013.01)

(58) Field of Classification Search
CPC .............. A61B 5/6824; A61B 5/02422; A61B 5/14552; A61B 5/681; A61B 5/6838; A61B 2562/02; A61B 2562/146; A61B 5/145

See application file for complete search history.

(56) References Cited

U.S. PATENT DOCUMENTS

| | | | |
|---|---|---|---|
| 3,769,974 A | * | 11/1973 | Smart ................ A61B 5/02427 600/479 |
| 6,230,034 B1 | | 5/2001 | Messerschmidt et al. |
| 10,076,257 B2 | | 9/2018 | Lin et al. |
| 10,702,211 B2 | | 7/2020 | Clavelle et al. |

(Continued)

OTHER PUBLICATIONS

Final Office Action issued in U.S. Appl. No. 15/650,744, dated Nov. 29, 2019 in 10 pages.

(Continued)

*Primary Examiner* — Eric F Winakur
*Assistant Examiner* — Abid A Mustansir
(74) *Attorney, Agent, or Firm* — Kilpatrick Townsend & Stockton LLP (57) ABSTRACT

An integrated window for a photosensor for use in an electronic device has first and second transparent regions separated by an opaque region. The first transparent region allows a transmitter to emit light out of the housing of the electronic device and the second transparent region allows a receiver to receive light through the housing. The opaque region is disposed between the first and second transparent regions to isolate them from one another such that the transmitted light is isolated from the received light.

20 Claims, 9 Drawing Sheets

(56) References Cited

U.S. PATENT DOCUMENTS

| | | |
|---|---|---|
| 10,987,054 B2 | 4/2021 | Pandya et al. |
| 11,406,325 B2 | 8/2022 | Clavelle et al. |
| 11,474,483 B2 | 10/2022 | Rothkopf et al. |
| 2007/0027380 A1 | 2/2007 | DeLonzar et al. |
| 2007/0099328 A1 | 5/2007 | Chiang et al. |
| 2008/0006859 A1 | 1/2008 | Mionetto |
| 2009/0171177 A1 | 7/2009 | Hannula et al. |
| 2010/0056934 A1* | 3/2010 | Cho ............. A61B 5/681 600/502 |
| 2014/0206954 A1 | 7/2014 | Yuen et al. |
| 2014/0275949 A1* | 9/2014 | Takahashi ........ A61B 5/6824 600/407 |
| 2016/0089067 A1 | 3/2016 | Kanayama |
| 2017/0000350 A1* | 1/2017 | Kwon ............ A61B 5/0059 |
| 2018/0014781 A1 | 1/2018 | Clavelle et al. |

OTHER PUBLICATIONS

Non-Final Office Action issued in U.S. Appl. No. 15/650,744, dated May 16, 2019 in 9 pages.
Notice of Allowance issued in U.S. Appl. No. 15/650,744, dated Mar. 4, 2020 in 7 pages.
Non-Final Office Action issued in U.S. Appl. No. 16/900,045, dated Oct. 22, 2021 in 15 pages.
Notice of Allowance issued in U.S. Appl. No. 16/900,045, dated Apr. 11, 2022 in 8 pages.

\* cited by examiner

SENSOR WINDOW WITH INTEGRATED ISOLATION FEATURE

CROSS-REFERENCES TO OTHER APPLICATIONS

This application is a continuation of U.S. patent application Ser. No. 16/900,045, filed Jun. 12, 2020, which is a continuation of U.S. patent application Ser. No. 15/650,744, filed Jul. 14, 2017, which claims the benefit of and priority to U.S. Provisional Application No. 62/363,134, for "SENSOR WINDOW WITH INTEGRATED ISOLATION FEATURE" filed on Jul. 15, 2016 which is hereby incorporated by reference in entirety for all purposes.

FIELD

The described embodiments relate generally to transparent windows used by photoelectric physiological sensors (e.g., a heart rate sensor) employed in wearable electronic devices. More particularly, the present embodiments relate to windows that have two transparent regions with an opaque region disposed between the two transparent regions.

BACKGROUND

Currently there are a wide variety of wearable electronic devices that include one or more physiological sensors that can measure parameters such as, for example, heart rate, blood oxygen content, $CO_2$ levels, hydration levels, skin temperature, and galvanic skin response. Some physiological sensors can use photoelectric feedback (i.e., photosensors) and can include a photoemitter and a photodetector that collect information from the user's skin and/or underlying tissue. As wearable devices become smaller, more efficient and more accurate it can be desirable to have the photoemitter and photodetector as close together as possible while maintaining the necessary optical isolation within the wearable electronic device required for accurate readings.

SUMMARY

Some embodiments of the present disclosure relate to windows that are inserted within external housings of electronic devices that include photoelectric physiological sensors. The windows include at least two transparent regions separated by an opaque isolation region. One of the transparent regions allows a photoemitter disposed within the electronic device to transmit light through the window such that it impinges a user's skin and/or underlying flesh, while a second transparent region allows at least a portion of the light that gets reflected off the user's skin and/or underlying flesh to be received by a detector disposed within the electronic device. The reflected light can be analyzed by circuitry within the electronic device to determine one or more physiological parameters of the user.

In some embodiments a portable electronic device comprises a housing having an opening extending from an interior surface of the housing to an exterior surface of the housing and a photosensor window positioned within the opening. The photosensor window includes a first transparent region that allows light from a photoemitter positioned within the housing to pass through the opening, a second transparent region that allows light to pass through the opening and be received by a photodetector that is positioned within the housing, and an opaque region positioned between and optically isolating the first transparent region and the second transparent region.

In some embodiments the first transparent region is bonded to a first side of the opaque region and the second transparent region is bonded to a second side of the opaque region and wherein the first side is opposite and adjacent the second side. In various embodiments the first and second transparent regions comprise a first material and are bonded together with an opaque material that forms the opaque region.

In some embodiments the photosensor window comprises a monolithic component formed from a unitary material and wherein the opaque region comprises induced defects within the unitary material. In various embodiments the first and second transparent regions comprise a first material and the opaque region comprises a second material that is different from the first material. In some embodiments the housing includes a back cover that is secured to a casing and the opening is formed through the back cover. In various embodiments the first and second transparent regions comprise: sapphire, onyx, transparent plastic, alumina, silicon or silicon dioxide. In some embodiments the opaque region comprises: zirconia, alumina, black glass, glass frit, heat activated film, metal, a transparent material with induced defects or an opaque plastic.

In some embodiments a wearable electronic device comprises a housing including an interface region configured to be in contact with a user's skin and an opening is formed through the housing in the interface region. A physiological sensor is positioned within the housing and includes a photoemitter and a photodetector. A physiological sensor window is affixed within the opening and includes a first transparent region positioned adjacent the photoemitter allowing light from the photoemitter to be transmitted through the opening, a second transparent region positioned adjacent the photodetector and allowing light to pass through the opening and be received by the photodetector, and an opaque region disposed between the first and the second transparent regions.

In some embodiments the first transparent region is bonded to a first side of the opaque region and the second transparent region is bonded to a second side of the opaque region and the first side is opposite and adjacent the second side. In various embodiments the first and second transparent regions comprise a first material and are bonded together with an opaque material that forms the opaque region. In some embodiments the physiological sensor window comprises a monolithic component formed from a unitary material and wherein the opaque region comprises induced defects within the unitary material. In various embodiments the first and second transparent regions comprise a first material and the opaque region comprises a second material that is different from the first material.

In some embodiments the housing includes a back cover attached to a casing and the opening is formed through the back cover. In various embodiments the first and second transparent regions comprise: sapphire, onyx, transparent plastic, alumina, silicon or silicon dioxide. In some embodiments the opaque region comprises: zirconia, alumina, black glass, glass frit, heat activated film, metal, a transparent material with induced defects or an opaque plastic.

In some embodiments a portable electronic device comprises a housing including a transparent wall and an electronic assembly enclosed within the housing and including a photoemitter and a photodetector positioned adjacent the transparent wall. One or more opaque channels are formed within the transparent wall to a depth of at least one-half a thickness of the transparent wall and are positioned between a photoemitter region and a photodetector region of the transparent wall.

In various embodiments the photoemitter is aligned with the photoemitter region of the transparent wall and the photodetector is aligned with the photodetector region of the transparent wall. In some embodiments the one or more opaque channels include a first opaque channel that encircles the photoemitter region of the transparent wall and extends through the thickness of the transparent wall. In various embodiments the one or more opaque channels include a first opaque channel that encircles the photodetector region of the transparent wall and extends through the thickness of the transparent wall.

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evident to the contrary from the description, where elements in different figures use identical reference numbers, the elements are generally either identical or at least similar in function or purpose.

DETAILED DESCRIPTION

Some embodiments of the present disclosure relate to windows that are inserted within external housings of electronic devices that include photoelectric physiological sensors. The windows include at least two transparent regions separated by an opaque isolation region. One of the transparent regions allows a photoemitter disposed within the electronic device to transmit light through the window such that it impinges a user's skin and/or underlying flesh, while a second transparent region allows at least a portion of the light that gets reflected off the user's skin and/or underlying flesh to be received by a detector disposed within the electronic device. The reflected light can be analyzed by circuitry within the electronic device to determine one or more physiological parameters of the user.

Some embodiments relate to a single window with an opaque isolation region formed within it while other embodiments relate to two windows disposed within an opaque substrate. Various embodiments provide methods of integrating windows within a wearable electronic device providing a mechanically sound and robust seal from moisture and dust intrusion. While the present disclosure can be useful for a wide variety of configurations, some embodiments of the disclosure are particularly useful for windows employed in wearable electronic devices that enable an internally mounted photosensor to monitor a user's physiological information such as blood oxygen content, $CO_2$ levels and/or heart rate.

In order to better appreciate the features and aspects of windows that have an integrated opaque isolation region according to the present disclosure, further context for the disclosure is provided in the following section by discussing one particular implementation of a wearable electronic device according to embodiments of the present disclosure. These embodiments are for example only and other embodiments can be employed in other electronic devices such as, but not limited to mobile phones, computers, all types of wearable electronic devices, media players and other devices.

Figure 1A:
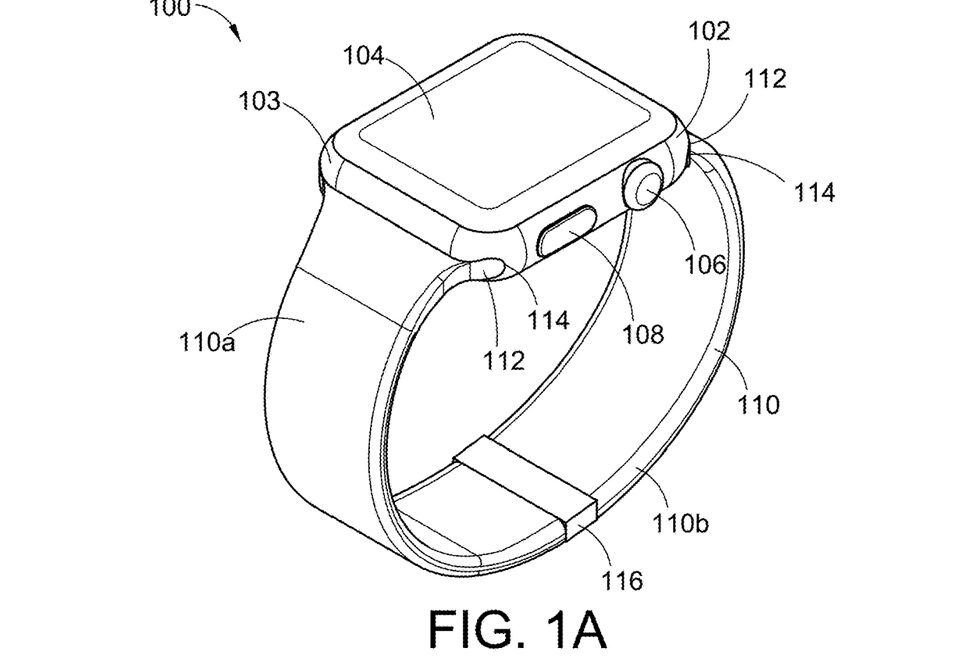
FIGS. 1A and 1B are isometric views of a wearable electronic device that includes a one or more photoelectric sensors according to embodiments of the disclosure.
Figure 1B:
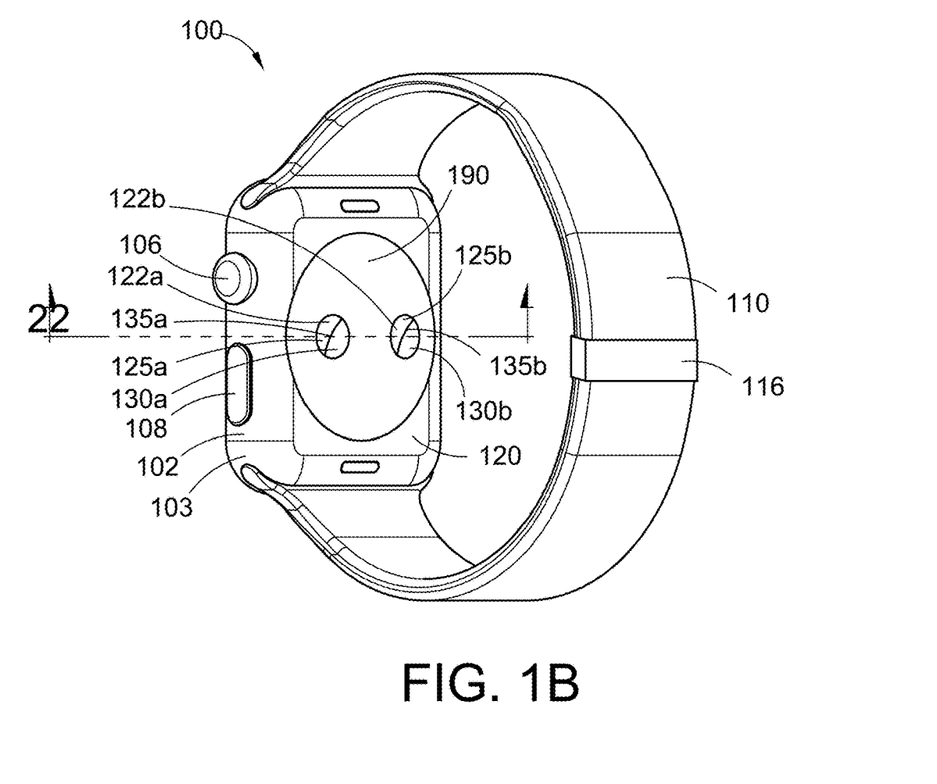

Reference is now made to FIGS. 1A and 1B, that depict front and rear perspective views of one type of wearable electronic device 100 that includes one or more photosensors to monitor a user's physiological information. As shown in FIGS. 1A and 1B wearable electronic device 100 can have one or more photosensor windows 122a, 122b with each window having integrated opaque isolation regions, as discussed in more detail below.

Wearable electronic device 100 includes a housing 102 that is attached to a display window 104 and includes various input devices that, in the embodiment depicted, can include a dial 106 and a button 108. Wearable electronic device 100 can be worn on a user's wrist and secured thereto by a band 110. Band 110 includes first and second band segments 110a, 110b, each of which is coupled to a lug 112 at one end of each band segment and that fits within a respective recess or aperture 114 of housing 102 allowing each band segment 110a, 110b to be removably attached to wearable electronic device 100.

In the embodiment illustrated in FIGS. 1A and 1B, housing 102 can include a separate back cover 190 that is secured to a casing 103. Casing 103 can be made from a metal, ceramic, glass or plastic material and have openings configured to receive display window 104 and back cover 190. In embodiments that use inductive charging to recharge wearable electronic device 100, back cover 190 can be made out of a ceramic, glass or plastic material, as described in more detail below, to provide a low resistance path for inductive charging. However, in embodiments that do not use inductive charging, back cover 190 can be made from any material, including a metal. In some embodiments, wearable electronic device 100 may not have a separate back cover and housing 102 can be a unitary structure with an opening to receive display window 104 that is positioned opposite a continuous bottom surface 120. In embodiments without a back cover that use inductive charging, housing 102 can be made from a ceramic, glass or plastic material. However in embodiments without a back cover that do not use inductive charging, housing 102 can be made from any material including a metal.

First and second photosensor windows 122a, 122b, respectively, that can also be referred to as inserts, are fit within openings formed in housing 102 and are exposed on bottom surface 120 of the housing. The openings extend from an interior surface of housing 102 to an exterior surface of the housing and therefore first and second photosensor windows 122a, 122b, respectively, allow light to pass through the housing. These features are shown in detail in FIGS. 2A and 2B. As discussed above, in some embodiments housing 102 can include a back cover 190 and the openings can be formed in the back cover.

First and second photosensor windows 122a, 122b, respectively, enable photosensors (not shown in FIG. 1A or 1B) within housing 102 to monitor a user's physiological information such as blood oxygen content, $CO_2$ levels and heart rate by collecting information from the user's skin and/or underlying tissue. According to some embodiments of the disclosure, either or both of photosensor windows 122a, 122b can include first and second transparent regions separated by an opaque region. For example, photosensor window 122a can include a first transparent region 125a that allows transmitted light from the respective photosensor to impinge the user's skin and a second transparent region 130a that allows light reflected off the user's skin and/or underlying tissue to be received by the photosensor. A first opaque region 135a can be disposed between first and second transparent regions, 125a, 130a, respectively, to isolate the transmitted light from the reflected light so the reflected light primarily comes from the user and not from within first photosensor window 122a.

Similarly, second photosensor window 122b can include two transparent regions 125b, 130b separated by a second opaque region 135b. Second photosensor window 122b can be used in a similar fashion as first photosensor window 122a. In some embodiments first photosensor window 122a can be used for a first type of physiological sensor and second photosensor window 122b can be used for a different type of physiological sensor. For example, in one embodiment a first photosensor employs a first wavelength of light and window 122a has transparent regions that are transparent to the first wavelength. Similarly, a second photosensor employs a second wavelength of light different from that of the first photosensor and window 122b has transparent regions that are transparent to the second wavelength. The photosensors, first and second photosensor windows 122a, 122b, and the function of one particular type of photosensor will be discussed in more detail below.

Wearable electronic device 100 includes circuitry, sensors, one or more electronic assemblies, display and input devices (not all shown in FIGS. 1A and 1B) that enable it to perform a variety of functions including, but not limited to: keeping time; monitoring a user's physiological signals and providing health-related information based on those signals; communicating (in a wired or wireless fashion) with other electronic devices; providing alerts to a user, which can include audio, haptic, visual and/or other sensory output, any or all of which can be synchronized with one another; visually depicting data on a display; gathering data from one or more sensors that can be used to initiate, control, or modify operations of the device; determining a location of a touch on a surface of the device and/or an amount of force exerted on the device, and use either or both as input; accepting voice input to control one or more functions; accepting tactile input to control one or more functions; and so on.

Figure 2A:
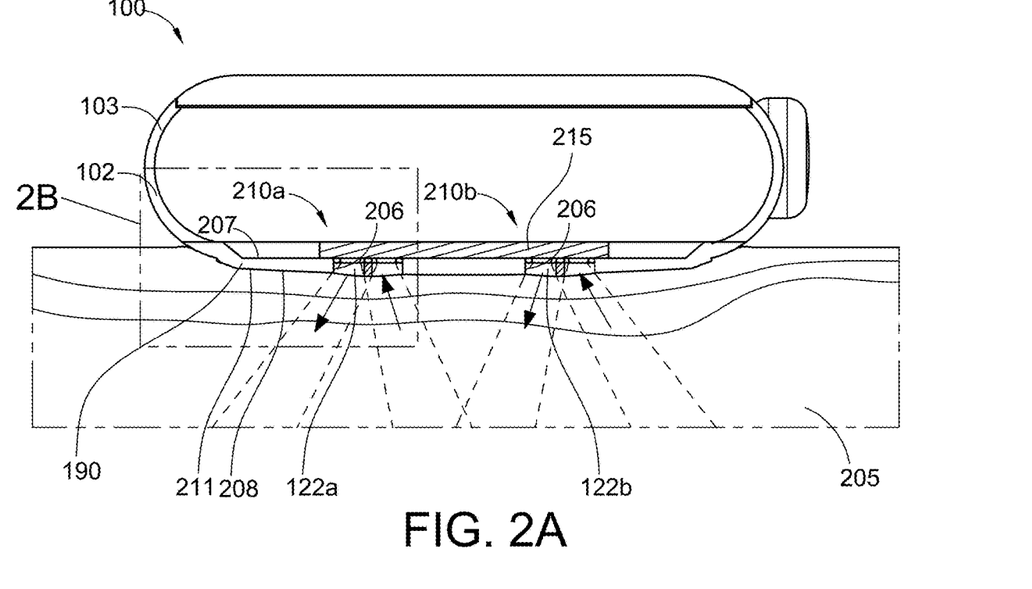
FIG. 2A illustrates a simplified partial cross-sectional view of the wearable electronic device illustrated in FIGS. 1A and 1B, fitted on a portion of a user's wrist.

FIG. 2A illustrates a simplified partial cross-sectional view of wearable electronic device 100 illustrated in FIGS. 1A and 1B, fitted on a portion of a user's wrist such that it is in contact with user's skin 205. As shown in FIG. 2A, first and second photosensor windows 122a, 122b allow first and second photosensors 210a, 210b, respectively, to acquire physiological data from user's skin 205 and/or underlying flesh. First and second photosensor windows 122a, 122b are disposed within openings 206 that extend through housing 102 from an interior surface 207 to an exterior surface 208 that forms an interface region 211 with user's skin 205. First and second photosensors 210a, 210b, respectively, can be secured to a substrate 215 that can be a circuit board or other structure. First photosensor 210a is positioned over first photosensor window 122a and second photosensor 210b is positioned over second photosensor window 122b.

Figure 2B:
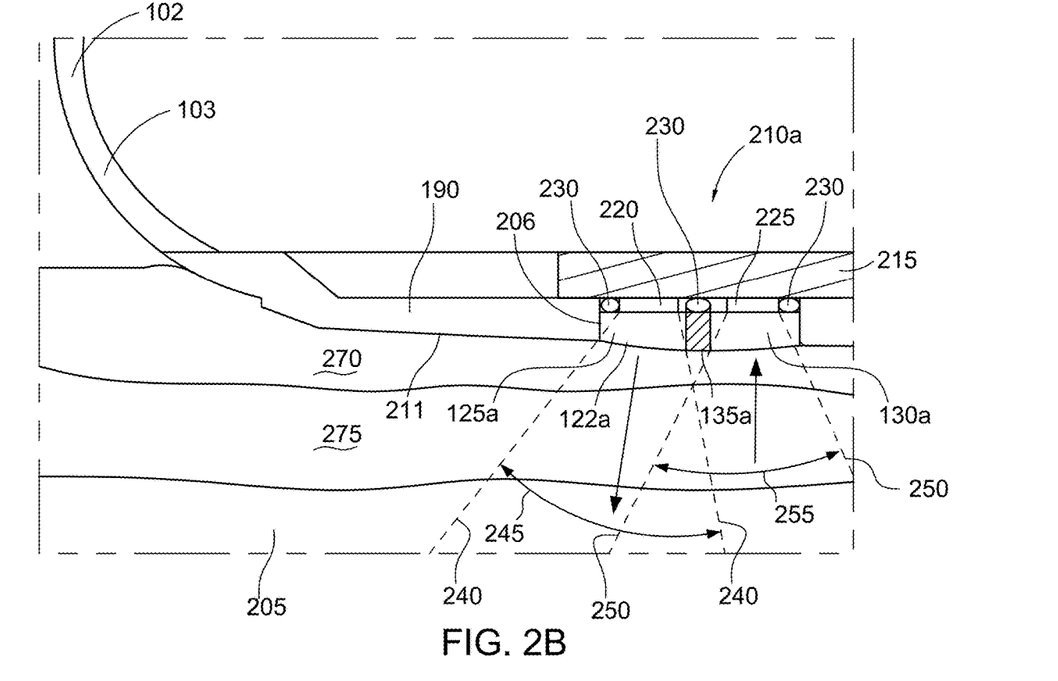
FIG. 2B illustrates an enlarged partial view of a portion of the wearable electronic device illustrated in FIG. 2A.

FIG. 2B illustrates an enlarged partial view of a portion of the wearable electronic device illustrated in FIG. 2A. As shown in FIG. 2B, first photosensor 210a can include a photoemitter 220 and a photodetector 225. In some embodiments an opaque sealant 230 can be placed between photoemitter 220 and photodetector 225 such that light cannot pass from the photoemitter to the adjacent photodetector. Opaque sealant 230 can also be disposed entirely around a perimeter of photoemitter 220 and photodetector 225.

First photosensor 210a is positioned over first photosensor window 122a such that photoemitter 220 is positioned over first transparent region 125a so it can emit light outside of housing 102 and impinge user's skin 205 and/or underlying tissue. Photodetector 225 is positioned over second transparent region 130a so it can receive light reflected from user's skin 205 and/or underlying tissue. First opaque region 135a is positioned within first photosensor window 122a such that light from photoemitter 220 is not received by photodetector 225 through first photosensor window 122a. More specifically, first opaque region 135a maintains isolation between photoemitter 220 and photodetector 225 so that only light that has passed through user's skin 205 and/or underlying tissue is received by photodetector 225. Generally speaking, only light that has passed through a user's skin contains physiological information from the user and all other light, such as light that can leak through first photosensor window 122a is considered noise that degrades signal quality. Dashed lines 240 illustrate a transmit angle 245 for photoemitter 220 and dashed lines 250 illustrate a receive angle 255 for photodetector 225. Transmit angle 245 and receive angle 255 are controlled by the interface of first photosensor window 122*a* with back cover 190 and with first opaque region 135*a*.

In one embodiment first photosensor 210*a* can be used as a portion of a circuit to perform photoplethysmography on user's skin 205 and/or underlying tissue to determine their heart rate. A photoplethysmography sensor is based on the fact that blood is red because it absorbs green and blue light. Therefore, photoemitter 220, which can be a light emitting diode, can use green light (e.g., light that exists predominantly in the green portion of the spectrum) to impinge the user's skin. Photodetector 225, which can be a photodiode, can be used to detect the amount of green light that is transmitted through the user's skin. The amount of green light received can be correlated to the amount of blood flowing through user's skin 205 and/or underlying tissue at any given moment. When the user's heart beats, the blood flows in their skin 205 and/or underlying tissue and the green light absorption is greater (i.e., photodetector 225 receives less green light).

Between heartbeats the green light absorption is less because there is less blood in user's skin 205 and/or underlying tissue. By flashing photoemitter 220, sometimes up to hundreds of times per second, and isolating the associated light signals at photodetector 225, the photosensor signal can be used to calculate the number of times the user's heart beats each minute. First photosensor 210*a* can also be designed to compensate for low signal levels by increasing both photoemitter 220 brightness and sampling rate, among varying other parameters. This is only one example of a photosensor that can use a photosensor window including an integrated opaque isolation barrier, other sensors and applications are within the scope of this disclosure.

In some embodiments a single photosensor window, such as first photosensor window 122*a*, having an integrated opaque region can enable a reduction in size of the associated electronic device, a more aesthetically pleasing design, lower power consumption and/or improved accuracy, as discussed in more detail below.

In one example, first opaque region 135*a* integrated in a single window, such as first photosensor window 122*a*, can enable photoemitter 220 and photodetector 225 to be placed closer together than they could be placed if two separate windows were used in the electronic device. The closer spacing can enable the electronic device to be more compact since less space is required for the windows and/or photosensor. The reduction in the number of required windows through the case of the electronic device can also improve the aesthetics of the electronic device since fewer windows require fewer disruptions and discontinuities in the external housing of the electronic device.

Further, the closer spacing between photoemitter 220 and photodetector 225 can enable a reduction in power consumption of the photosensor by reducing the amount of distance the photoemitter has to transmit light to be detected by the photodetector, therefore requiring less power from the phototransmitter to achieve a desired signal strength at the photodetector. More specifically, the shorter the distance the light has to travel through the user's skin and/or underlying flesh, the less power that is required from the photoemitter to achieve a desired signal strength at the photodetector.

In another example, a photosensor window including transmit and receive regions with an integrated opaque region, such as first photosensor window 122*a*, can exhibit improved accuracy as compared electronic devices that have separate windows for transmitting and receiving the light signals. More specifically, still referring to FIG. 2B, for first photosensor 210*a* to accurately sense the time variant blood within user's skin 205 (e.g., skin) and/or underlying tissue, the user must have both the transmit and the receive windows in direct and intimate contact with their skin, preferably with enough force to push the window into their skin so that it displaces not only arterial blood 270, but also a substantial amount of lower-pressure venous blood 275.

When two separate and isolated windows are used, the two windows likely have a larger combined surface area than a single integrated window, such as first photosensor window 122*a*, so a user will have to push with more force to adequately displace venous blood 275 within their skin. If the user does not push with adequate force, the accuracy of the photoplethysmography sensor can be reduced. Additionally, when two separate and isolated windows are used it can be more difficult to maintain consistent contact of the two separate windows with the user's skin as compared to one smaller integrated window, such as first photosensor window 122*a*. Further, in electronic devices that only have one physiological sensor, an single integrated window can be located proximate the center of back cover 190 (see FIGS. 1B and 2A) making it more likely to remain in contact with the user during use.

As discussed above, in some embodiments a photodetector is used to detect the light emitted by the photoemitter. In various embodiments a photodiode can be used as a photodetector. A photodiode is a semiconductor device that converts light into electrical current. The current is generated when photons are absorbed in the photodiode. In some embodiments the photodiode can contain optical filters, built-in lenses, and can have large or small surface areas. In other embodiments a different type of photodetector can be used and is within the scope of this disclosure.

As discussed above, in some embodiments a photoemitter can be used to emit light that is received by a photodetector. In the example above a green LED was used as a photoemitter, however other types and wavelengths of photoemitters can be used, which are all within the scope of this disclosure. For example, some embodiments can use photoemitters that emit red light between 600-750 nm, infrared light between 850-1000 nm and/or green light between 495-570 nm.

As discussed above a window having two transparent regions with an integrated opaque isolation region can be used to enable an associated photosensor to interact with a user's skin. As used herein, transparent shall mean transparent with regard to the wavelengths of the photoemitter and/or photodetector, which may or may not be the same wavelengths as visible light. More specifically, the transparent regions of the photosensor windows may only be transparent to the wavelengths of the photosensor, and the windows may or may not be transparent to an observer using only the visible spectrum. Accordingly, in some embodiments the transparent regions of the photosensor windows can be made from, for example, sapphire, onyx, plastic, alumina, silicon or silicon dioxide. In various embodiments the wavelength that one or more of the windows is transparent to can be red light between 600-750 nm, infrared light between 850-1000 nm and green light between 495-570 nm. In some embodiments one or more optical coatings can be used on one or more of the photosensor windows to reduce reflected light and/or filter the light that is emitted and/or received through the photosensor window. As used herein, transparent shall also mean that the material passes at least a portion of the photoemitter's light, regardless of the material's clarity. For example, the windows can be translucent, or can be made to distort the image of the elements behind them while still passing at least a portion of the photoemitter's light.

As used herein, opaque shall mean opaque with regard to the wavelengths of the photoemitter and/or photodetector, which may or may not be the same wavelengths as visible light. More specifically, the opaque regions of the photosensor windows may only be opaque to the wavelengths of the photoemitter and photosensor, thus the windows may or may not be opaque to an observer using only the visible spectrum. However in other embodiments the opaque region can also be opaque to visible light. Accordingly, in some embodiments the opaque regions of the window can be made from, for example, zirconia, alumina, black glass, glass frit, heat activated film, metal, a transparent material with induced defects and/or a plastic. In some embodiments the use of the term opaque shall mean that the material blocks a majority of the light energy described above (e.g., greater than 50 percent), however in other embodiments the material can block more than 75 percent of the light. In further embodiments the material can block at least 99 percent of the light and in yet further embodiments it can block at least 99.9 percent of the light. In various embodiments the material can block at least 99.99 percent of the light.

Figure 3:
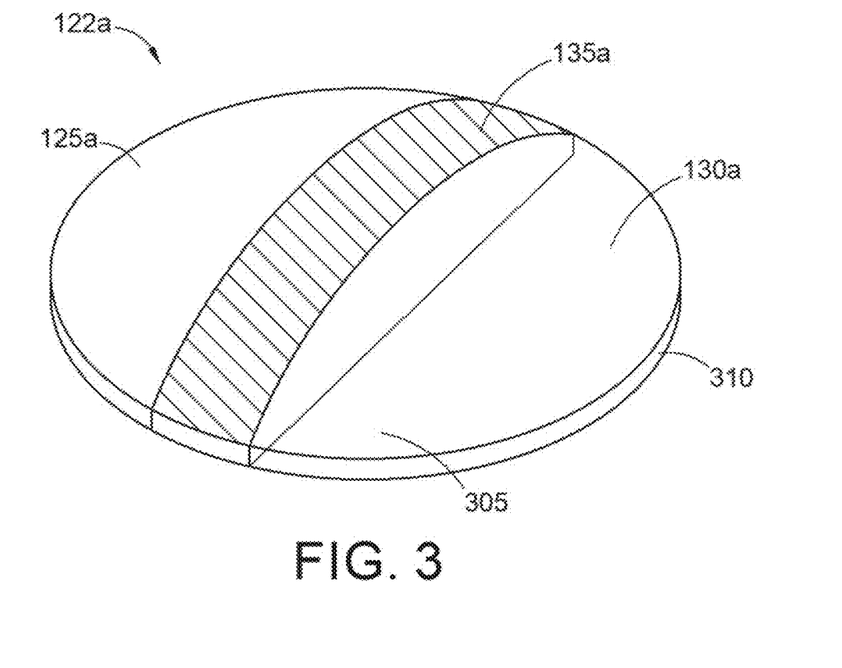
FIG. 3 illustrates a simplified perspective view of a first photosensor window that is used in the wearable electronic device illustrated in FIGS. 1A-2.

FIG. 3 illustrates a simplified perspective view of first photosensor window 122a, used in wearable electronic device 100 illustrated in FIGS. 1A-2B. As shown in FIG. 3, first photosensor window 122a can include first opaque region 135a disposed between first and second transparent regions, 125a, 130a, respectively. In some embodiments, exterior surface 305 can be contoured and shaped before assembling the window into back cover 190 (see FIG. 1B). In some embodiments exterior surface can be flat, convex or any other shape. A convex shape can enable improved contact with the user's skin and can be more comfortable for the user than other shapes. A perimeter 310 of first photosensor window 122a can be flat (e.g., not convex) to enable the window to be mounted within back cover 190 and to facilitate polishing and finishing without creating sharp edges that are prone to fracture. First opaque region 135a can be disposed between first and second transparent regions, 125a, 130a, respectively, using myriad manufacturing methods, some of which are described in more detail below.

Now referring to FIGS. 4-14 several example manufacturing methods for photosensor windows having an integrated opaque region are illustrated, however this disclosure is not limited to these methods and encompasses other methods that result in a similar structure having first and second transparent regions separated by an integrated opaque region.

Figure 4A:
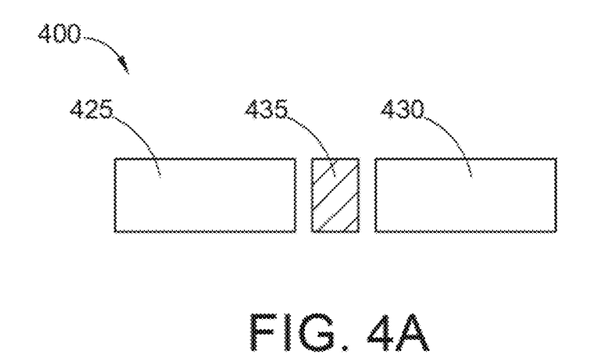
FIGS. 4A and 4B illustrate steps associated with a method of forming a photosensor window having an integrated opaque region.
Figure 4B:
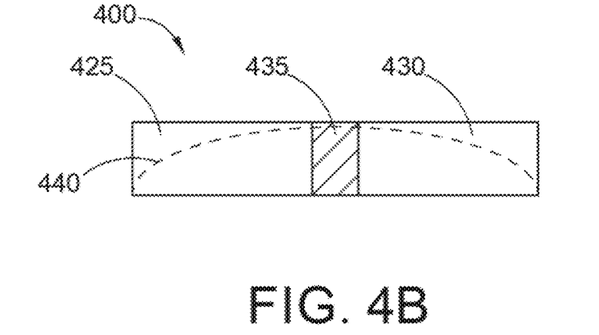

FIGS. 4A and 4B illustrate steps associated with a method of forming a photosensor window 400, that can be similar to first photosensor window 122a, having an integrated opaque region. As shown in FIGS. 4A and 4B, first and second transparent regions 425, 430, respectively, are affixed to an opaque region 435. The final structure is then ground or shaped into a photosensor window that can resemble first photosensor window 122a illustrated in FIG. 3. More specifically, one or more exterior surfaces of the bonded structure (shown in in FIG. 4B) can be shaped and/or polished (illustrated by dashed line 440 in FIG. 4B) to achieve the final geometry and finish required by wearable electronic device 100 (see FIG. 1). In some embodiments the bonded structure can be shaped using machining, polishing, chemo-mechanical grinding, laser ablation, abrasive media blasting or other method. Final polishing can be performed with media tumbling, vibratory media finishing, abrasive media blasting, polishing or other method. In various embodiments, photosensor window 400 can be first integrated into back cover 190 (see FIG. 1B), then shaped and/or polished along with the back cover to achieve a unified appearance.

In one example first and second transparent regions 425, 430, respectively, are made from onyx and are brazed to opaque region 435 that is made from zirconia. Brazing can be performed with a material having a glass frit or other binder that bonds directly to the onyx and zirconia. In another example the faying surfaces of first and second transparent regions 425, 430, respectively and opaque region 435 can be metallized and the metallized surfaces can be brazed together using a metal or alloy.

The substitution of other materials for first and second transparent regions 425, 430 in the manufacturing process described above is within the scope of this disclosure. For example, silicon dioxide can be used for first and second transparent regions 425, 430 respectively, and black glass can be used for opaque region 435. Further, other methods of bonding the first and second transparent regions 425, 430 respectively, to opaque region 435 are within the scope of this disclosure. For example, a heat activated film, a glue, an epoxy or other material can be used to bond the materials together. In some embodiments a gap fill can be applied to regions of the interface between first and second transparent regions 425, 430, respectively, and opaque region 435 to seal the external surface of the wearable electronic device and to protect the underlying bonding material. More specifically, if a bonding material is used to bond materials together, a gap fill that has improved environmental resilience can be applied to the outside of the joint to protect the bonding material from environmental degradation.

In some embodiments FIGS. 4A and 4B can also be illustrative of a manufacturing process that can be used with fused glass where first and second transparent regions 425, 430, respectively, are made from glass (e.g., silicon dioxide) and are fused to opaque region 435 made from black glass. Black glass can be any type of glass material having one or more dopants that make it opaque to the wavelengths of the photoemitter and photodetector. Under high temperature and possibly under pressure, first and second transparent regions 425, 430, respectively, and opaque region 435, can be fused together forming a monolithic structure. The final structure can be shaped and polished as discussed above with regard to FIG. 4B. Any materials disclosed within this application can be substituted for the glass and the black glass materials for the fusing process described above and such embodiments are within the scope of this disclosure.

In some embodiments FIGS. 4A and 4B can also be illustrative of a process that can be used to co-sinter first and second transparent regions 425, 430, respectively, with opaque region 435. In this process first and second transparent regions 425, 430, respectively, and opaque region 435 can begin the manufacturing process in a "green" state where each material includes particles held together with a binder. The materials are pressed together and co-sintered at a high temperature to burn off the binder and fuse the particles together resulting in a monolithic fused structure. In one example illustrated by FIG. 4A, first and second transparent regions 425, 430, respectively, are made from green state alumina (i.e., $Al_2O_3$ particulates held together by a binder) and opaque region 435 is made from green state zirconia (i.e., $ZrO_2$ particulates held together by a binder). In FIG. 4B, first and second transparent regions 425, 430, respectively, and opaque region 435 are pressed together and co-fired at high temperatures resulting in a co-sintered structure. The structure can be shaped and polished as discussed above with regard to FIG. 4B resulting in window that can be similar to first photosensor window 122a in FIG. 3. The substitution of other materials for the alumina and zirconia materials for the co-sintering process described above is within the scope of this disclosure.

The various manufacturing methods described above with regard to FIGS. 4A and 4B can be used to provide a high degree of accuracy and control over the separation of first and second transparent regions 425, 430, since the separation is predominantly governed by a width of opaque region 435. The accuracy and control over the separation can enable a repeatable manufacturing process that maintains a consistent portion of the user's skin that the light must travel through and as a result consistent performance of the photosensor.

Figure 5A:
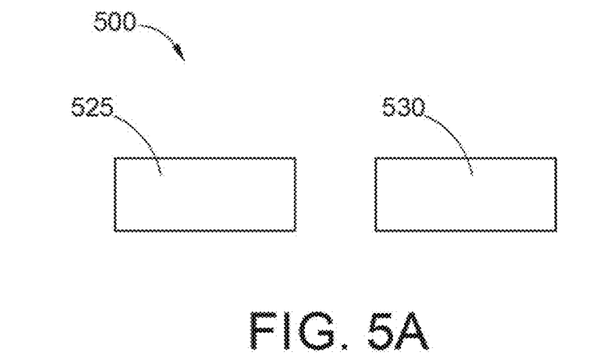
FIGS. 5A and 5B illustrate steps associated with a method of forming a photosensor window having an integrated opaque region.
Figure 5B:
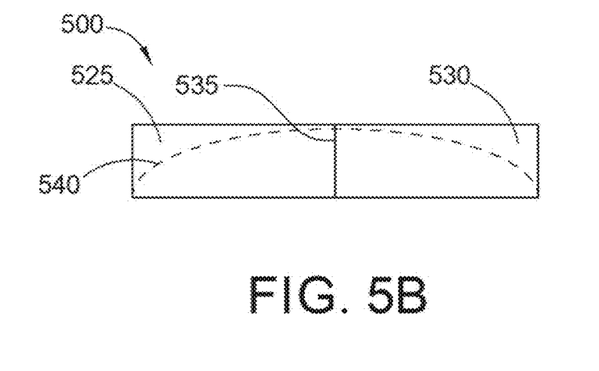

FIGS. 5A and 5B illustrate steps associated with a method of forming a photosensor window 500 having an integrated opaque region. As show in FIGS. 5A and 5B first and second transparent regions 525, 530, respectively, can be joined together while forming an opaque region 535 in the process. Method 500 is somewhat similar to the process described above in FIGS. 4A and 4B, however in method 500 opaque region 535 is not a separate component that is bonded between the two transparent regions; it is a result of joining the two transparent regions together. In one example, first and second transparent regions 525, 530, respectively, are made from onyx or glass and can be brazed together with a glass frit or other binder that bonds directly to the onyx or glass. The brazing material can be selected from a particular material that forms an opaque layer, isolating first and second transparent regions 525, 530, respectively, from one another. The resulting structure can then be shaped and/or polished to the desired final shape of the window (shown by line 540 in FIG. 5B), and as discussed above.

In a further example, the faying surfaces of first and second transparent regions 525, 530, respectively, can be metallized and brazing can be performed with a metal or alloy. The metallization and brazing form opaque region 535 that that isolates first and second transparent regions 525, 530, respectively, from one another. After brazing the surfaces of the bonded structure can be shaped and/or polished along line 540 to achieve the final geometry and finish as discussed above. The substitution of other materials for the onyx or glass materials for the brazing process described above is within the scope of this disclosure.

In some embodiments other methods of bonding the first and second transparent regions 525, 530, respectively, together are within the scope of this disclosure. For example, a heat activated film, a glue, an epoxy or other material can be used to bond first and second transparent regions 525, 530 together and simultaneously form an opaque region 535. The faying surfaces of first and second transparent regions 525, 530, respectively, may or may not be metallized. In one embodiment the faying surfaces are metallized with a material such as, for example, platinum that functions as a mirror providing an opaque region 535 that isolates first and second transparent regions 525, 530, respectively, from one another. The platinum surfaces are then bonded together with an adhesive or a brazing material.

In some embodiments if a metallic material such as metallization deposited on the faying surfaces or brazing material is used within the sensor window, it can be beneficial to ground the metal to wearable electronic device 100 (see FIG. 1A) ground. Grounding can be performed with a metallic trace formed across the sensor window, a wire, a flexible substrate or any other means. In other embodiments, the metallic region can be used for a charging contact or other function as described in more detail below.

Figure 6:
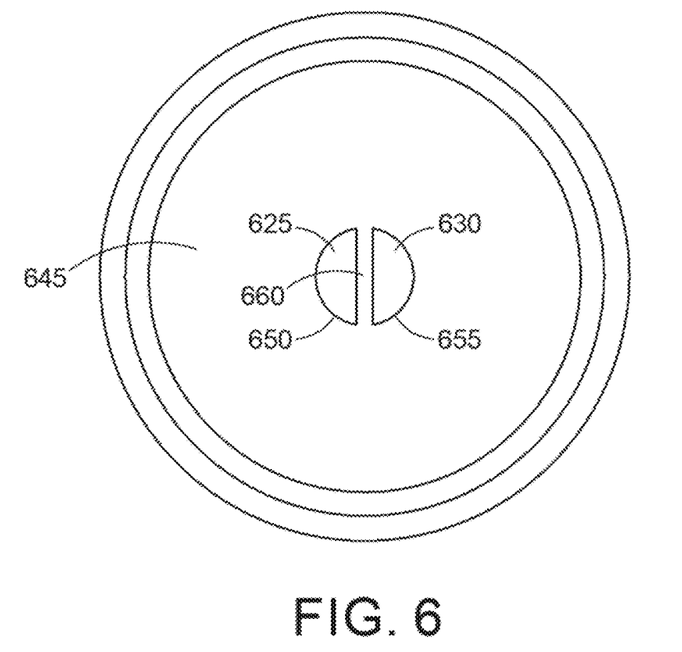
FIG. 6 illustrates a back cover that can be a component of wearable electronic device illustrated in FIGS. 1A and 1B, and includes first and second transparent windows.

FIG. 6 illustrates a back cover that can be a component of wearable electronic device 100 (see FIGS. 1A and 1B) and includes first and second transparent windows 625, 630, respectively. As shown in FIG. 6, back cover 645 can have two apertures, 650, 655, formed in it that receive first and second transparent windows 625, 630, respectively. A web 660 of back cover 645 is disposed between first and second transparent windows 625, 630, respectively, and forms an opaque region between the two transparent windows. In one embodiment opaque back cover 645 is a back portion of housing 102 (see FIG. 1A) and can be made of, for example, zirconia or a metal and two apertures 650a, 650b can be formed by casting, machining, cutting or other process. First and second transparent windows 625, 630, respectively, can then be fit within or formed within the apertures as described in more detail below.

In one example first and second transparent windows 625, 630, respectively, are formed from a transparent glass material that is cut to the shape of two apertures, 650, 655 and bonded in place with an epoxy, a heat activated film, a glass frit braze, a metallic braze or other material. In another example, first and second transparent windows 625, 630, respectively, can be fired in place within two apertures, 650, 655. More specifically, opaque back cover 645 can be heated such that it expands, a molten transparent glass can be used to fill two apertures, 650, 655, then the entire structure is cooled. Upon cooling the back cover material can be selected such that it shrinks faster than the glass within two apertures, 650, 655 such that it places the glass under compression to increase its strength. In one such embodiment opaque back cover 645 can be a metal and the glass can be silicon dioxide, however other embodiments can use different materials, such as those described within this disclosure. In various embodiments the coefficient of thermal expansion of the glass and the back cover can be matched and the bonding between them can be predominantly chemical in nature.

In some embodiments a glass sealing material can be used to bond first and second transparent windows 625, 630, respectively, into back cover 546. For example, a glass material (e.g., glass frit or solder glass) can be fired in around the periphery of sapphire windows to bond the sapphire windows within two apertures 650, 655. In some embodiments the glass material is selected to have a higher refractive index than the sapphire windows so the structure functions similar to an optical fiber having total internal reflection and thus good isolation between the photoemitter and photodetector. In some embodiments first and second transparent windows 625, 630, respectively, can have a tapered outer edge.

Figure 7:
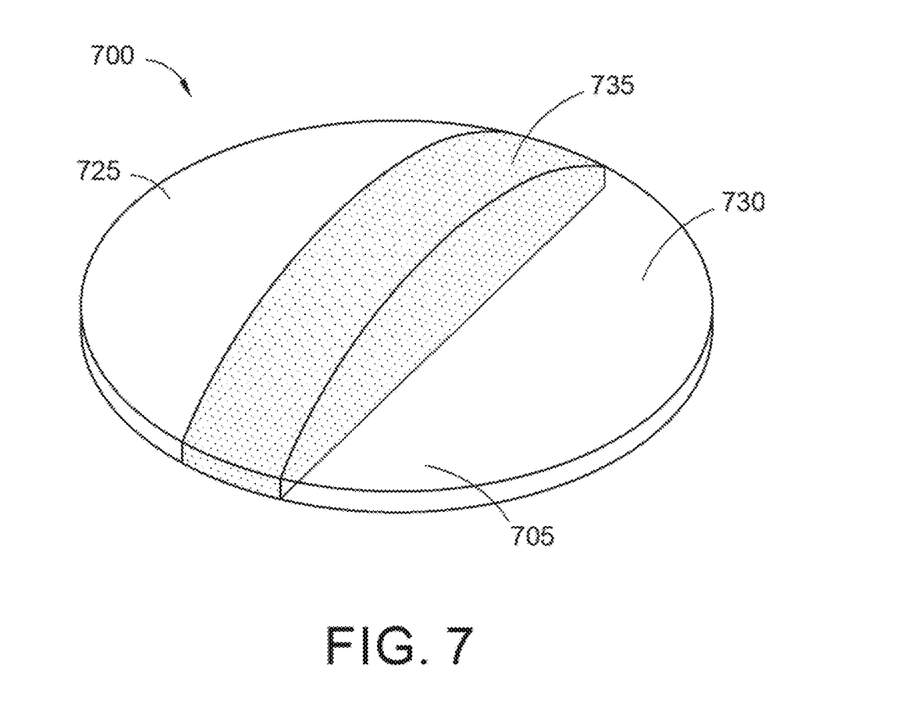
FIG. 7 illustrates a simplified isometric view of a photosensor window that can be used in the wearable electronic device illustrated in FIGS. 1A and 1B.

FIG. 7 illustrates a simplified isometric view of a photosensor window 700 that can be used in wearable electronic device 100 illustrated in FIGS. 1A and 1B. As shown in FIG. 7, photosensor window 700 can be a monolithic transparent component 705 that has an opaque region 735 formed by inducing defects within the material. Opaque region 735 forms an opaque barrier between first and second transparent regions 725, 730, respectively. In one example, monolithic transparent component 705 is made from onyx or other material. Opaque region 735 can be formed by inducing defects (e.g., damaging a region) within monolithic transparent component 705 with a laser such that opaque region 735 is formed throughout a thickness of photosensor window 700. Laser damaging can be performed with a laser that, for example, is used in laser direct structuring, 3-D laser engraving or the like. The induced defects can include, but are not limited to air voids, fractures and dislocations within the atomic lattice. Once opaque region 735 is sufficiently damaged to provide the necessary level of optical isolation, transparent photosensor window 700 can be annealed, chemically strengthened or processed in some other manner to strengthen the damaged area and/or improve the isolation properties of the damaged area.

In some embodiments, photosensor window 700 can be formed with two-shot plastic molding. That is, in a first injection molding operation first and second transparent regions 725, 730, respectively, can be formed by injecting a transparent plastic into a mold. The resulting components can be moved to a second molding station where an opaque region 735 can be formed between first and second transparent regions 725, 730, respectively. Opaque region 735 can be formed from an opaque plastic that forms an opaque layer isolating first and second transparent regions 725, 730, respectively, from one another. In various embodiments a similar process can be used to form photosensor window 700 by injecting transparent and opaque glass into one or more molds, rather than plastics into molds.

Figure 8:
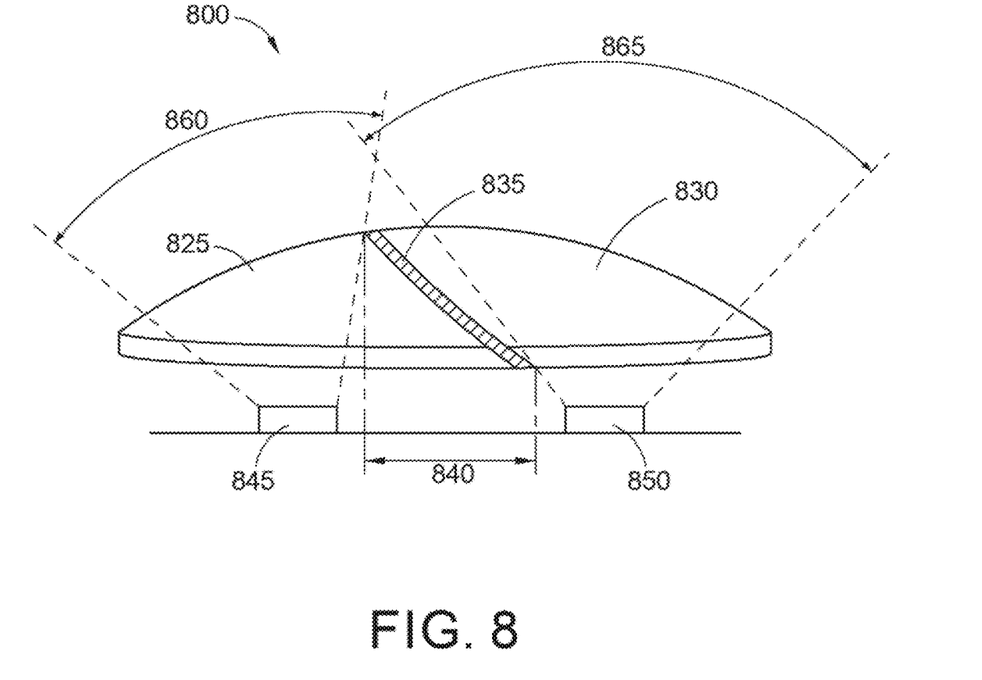
FIG. 8 illustrates a simplified cross sectional view of a photosensor window having a tilted opaque region and that can be used in the wearable electronic device illustrated in FIGS. 1A and 1B.

FIG. 8 illustrates a simplified cross sectional view of a photosensor window 800 having a tilted opaque region 835 and that can be used in wearable electronic device 100 (see FIGS. 1A and 1B). As shown in FIG. 8, tilted opaque region 835 can be used to isolate first and second transparent regions, 825, 830, respectively. Photosensor window 800 in FIG. 8 can be similar to photosensor window 122 illustrated in FIG. 2, however in the embodiment illustrated in FIG. 8, opaque region 835 is tilted, rather than oriented vertically. The tilting can be used to achieve a particular amount of separation distance 840 between a photoemitter 845 and a photodetector 850. The higher the degree of the tilt, the larger separation distance 840 becomes. The tilt can also enable a transmit angle 860 of photoemitter 845 and receive angle 865 of photodetector 850 to be adjusted such that they are unequal. Opaque region 835 can be tilted the opposite direction, inverting transmit angle 860 and receive angle 865. The tilted opaque region 835 can be used with any of the manufacturing concepts discussed herein.

Figure 9:
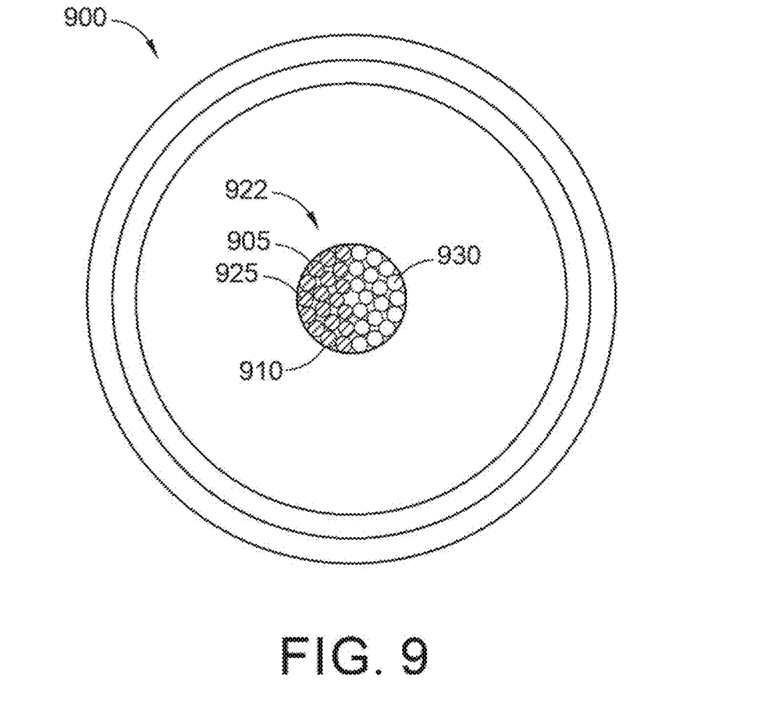
FIG. 9 illustrates a simplified plan view of a back cover including photosensor windows made from optical fiber and that can be used in the wearable electronic device illustrated in FIGS. 1A and 1B.

FIG. 9 illustrates a simplified plan view of a back cover 900 that can be used in wearable electronic device 100 (see FIGS. 1A and 1B). As shown in FIG. 9 a photosensor window 922 can be formed from a bundle of fiber optics 905 secured within an aperture 910 formed in back cover 900. More specifically, in one example a photoemitter can be positioned under a first group 925 of fibers forming a transmit region, and a photodetector can be positioned under a second group 930 of fibers forming a receive region. Since fiber optics internally reflect light energy within the fiber, once light enters first group 925 of fibers it will not bleed over to second group 930 of fibers. Therefore, the photoemitter and photodetector are optically isolated from one another. Fiber optics 905 can be secured within back cover 900 with an epoxy or other bonding material.

Figure 10:
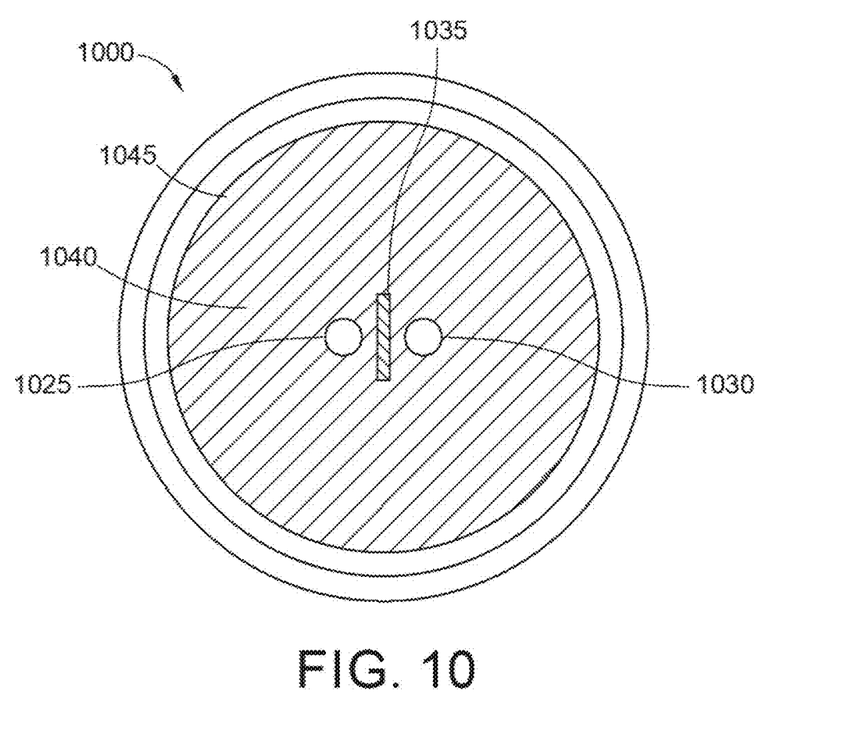
FIG. 10 illustrates a simplified plan view of a transparent back cover including an opaque mask and an opaque barrier that can be used in wearable electronic device 100 illustrated in FIGS. 1A and 1B.

FIG. 10 illustrates a simplified plan view of a back cover 1000 having opaque regions that can be used in wearable electronic device 100 (see FIGS. 1A and 1B). As shown in FIG. 10, back cover 1000 is made from a transparent material and opaque materials are used to isolate a photoemitter aperture 1025 from a photodetector aperture 1030. In one example, back cover 1000 can be made from a transparent material, such as glass. An opaque isolation barrier 1035 can be formed throughout a thickness of back cover 1000 by using a laser to damage the area or by removing the glass and filling the region with an opaque material, as discussed above. An opaque mask 1040 can be applied to a top surface 1045 of back cover 1000, forming a photoemitter aperture 1025 and a photodetector aperture 1030. Therefore, the combination of opaque mask 1040 and opaque isolation barrier 1035 can be used to maintain optical isolation between a photoemitter and a photodetector within back cover 1000.

Figure 11:
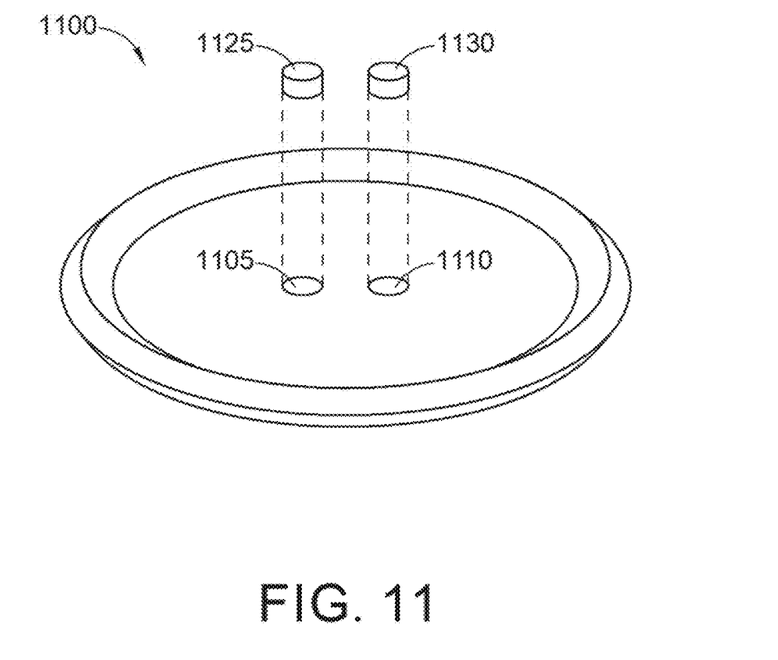
FIG. 11 illustrates a simplified perspective view of a back cover having one or more photosensor windows and that can be used in the wearable electronic device illustrated in FIGS. 1A and 1B.

FIG. 11 illustrates a simplified perspective view of a back cover 1100 having one or more photosensor windows and that can be used in wearable electronic device 100 (see FIGS. 1A and 1B). As shown in FIG. 11, back cover 1100 includes two transparent windows that are disposed within back cover 1100. Back cover 1100 in FIG. 11 is similar to back cover 645 illustrated in FIG. 6, however in this embodiment first and second transparent windows 1125, 1130, respectively, are fit within an opaque back cover 1100. In one embodiment opaque back cover 1100 is a back portion of housing 102 (see FIG. 1A) and can be made of, for example, zirconia or a metal and two apertures 1105, 1110 can be formed through a thickness of the back cover. First and second transparent windows 1125, 1130, respectively, can then be fit within or formed within two apertures 1105, 1110 using methods described in FIG. 6. In one example, a transparent glass material can be used for first and second transparent windows 1125, 1130, respectively, and bonded in place within two apertures 1105, 1110 with an epoxy, a heat activated film, a glass frit braze, a metallic braze or other material. In another example, first and second transparent windows 1125, 1130, respectively, can be fired in place.

Figure 12A:
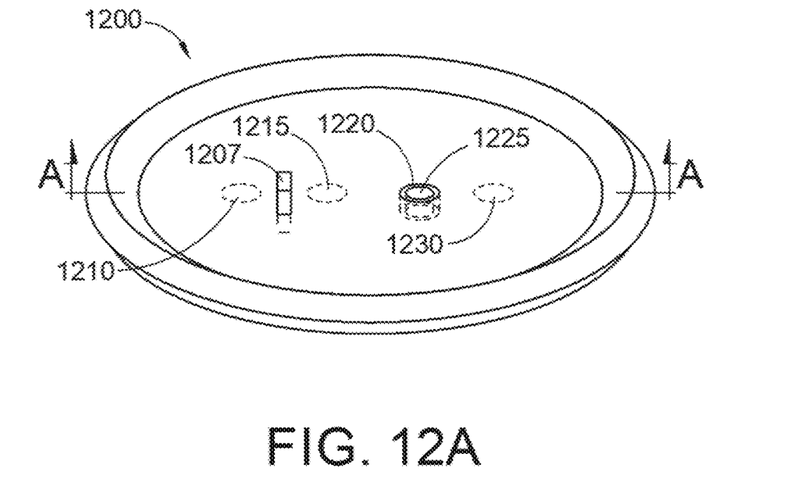
FIGS. 12A-12D illustrate steps associated with a method of forming optically isolated transparent windows in a transparent back cover that can be used in the wearable electronic device illustrated in FIGS. 1A and 1B.
Figure 12B:
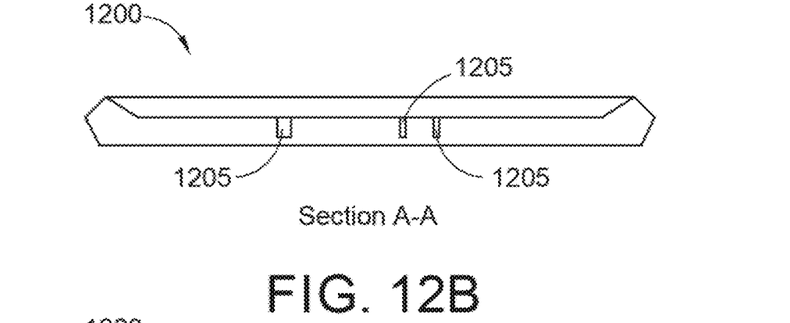
Figure 12C:
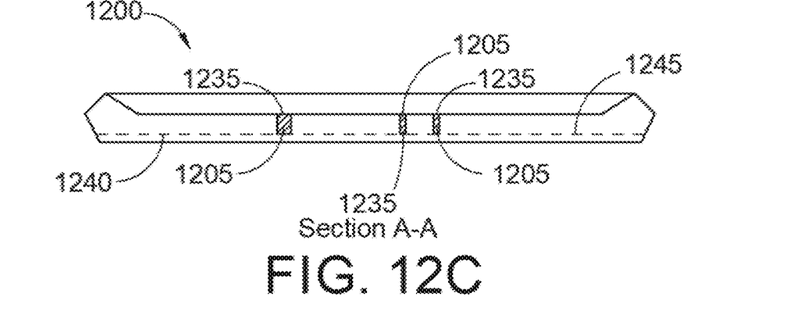
Figure 12D:
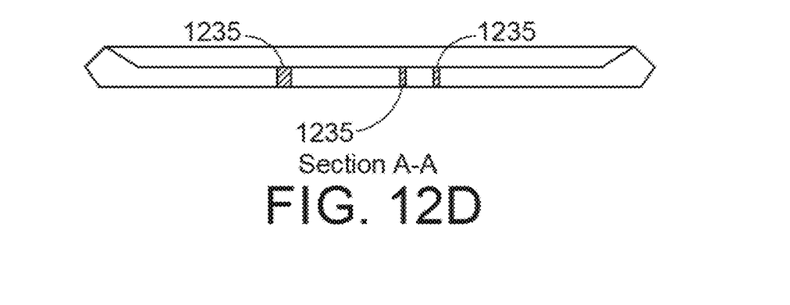

FIGS. 12A-12D illustrate steps associated with a method of forming optically isolated transparent windows in a transparent back cover 1200 that can be used in wearable electronic device 100 (see FIGS. 1A and 1B). As discussed above, transparent back cover 1200 can form a portion of housing 102 (see FIGS. 1A and 1B) of wearable electronic device 100 and therefore the transparent back cover can form a transparent wall of the housing. As shown in FIGS. 12A-12D an opaque material can be used to fill one or more channels formed within back cover 1200 to optically isolate regions of the back cover. FIG. 12A illustrates a simplified isometric view of back cover 1200 while FIGS. 12B-12D illustrate simplified cross-sectional views of back cover 1200 during each stage of the manufacturing process.

Now referring to FIG. 12B, one or more channels 1205 are formed in back cover 1200 to a depth of at least one half a thickness of the back cover. In one example transparent back cover 1200 is made from a glass. One or more channels 1205 can be formed within back cover 1200 by laser ablation, grinding, chemical etching, green state machining and post sintering or any other process. In some embodiments one or more channels 1205 are formed substantially through a majority of the thickness of back cover 1200, but are not formed entirely though (e.g., they are blind channels as shown in FIG. 12B). As shown in FIG. 12A, one or more channels 1205 can be any shape. In one example a straight channel 1207 can be used to separate a photoemitter region 1210 from a photodetector region 1215 while in another example a closed channel 1220 (e.g., such as a circle, octagon, square or other closed shape) can be used to completely enclose photoemitter region 1225, photodetector region 1230, or both.

Now referring to FIG. 12C, one or more channels 1205 are filled with an opaque material to form one or more opaque regions 1235. Any opaque material can be used to fill one or more channels 1205. In one embodiment the opaque material is a metallic braze that is fired into one or more channels 1205 and bonds to back cover 1200.

A back surface 1240 (shown in FIG. 12C) of back cover 1200 is removed (shown by dashed line 1245 in FIG. 12C) to a depth of one or more channels 1205 such that no transparent material remains at the bottom of the one or more channels. The final structure shown in FIG. 12D illustrates one or more opaque regions 1235 formed throughout the thickness of back cover 1200 providing optical isolation between photoemitter regions 1210,1225 and photodetector regions 1215, 1230 (see FIG. 12A).

In some embodiments where one or more opaque regions 1235 are formed from an electrically conductive material, the one or more opaque regions can be used as an electrically conductive feedthrough within back cover 1200. In one example, a pair of electrically conductive opaque regions can be used for charging and/or data contacts for wearable electronic device 100 (see FIG. 1A). In some embodiments back cover 1200 can have a thickness between 0.3 millimeters and 0.8 millimeters. In one embodiment a starting thickness of the back cover is approximately 0.7 millimeters and one or more channels 1205 are formed to a depth of 0.5 millimeters. After the channels are filled, approximately 0.2 millimeters of back surface 1240 of back cover 1200 is removed.

Figure 13:
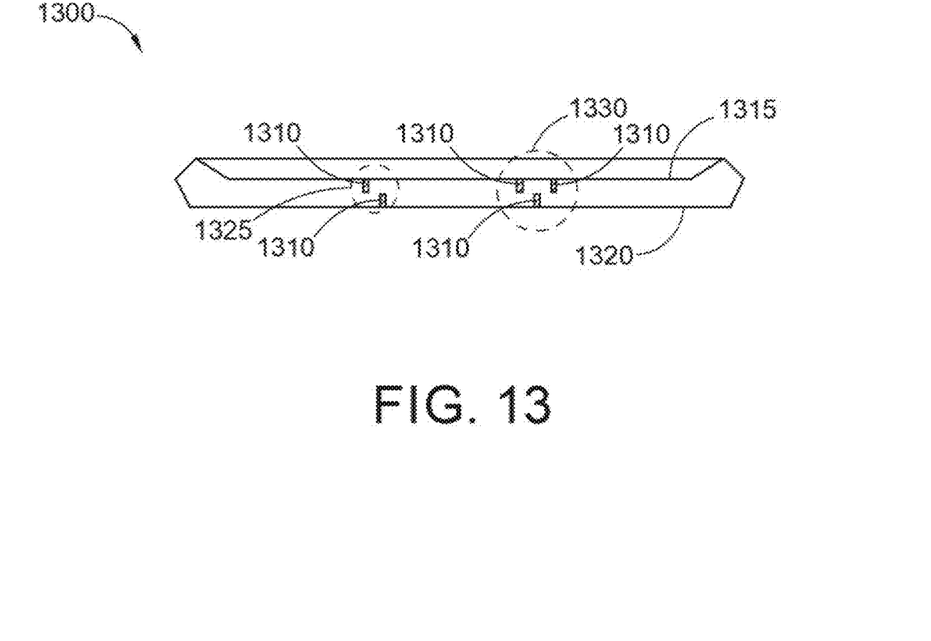
FIG. 13 illustrates a simplified cross-sectional view of a back cover that can be similar to the back cover illustrated in FIG. 12.

FIG. 13 illustrates a simplified cross-sectional view of a back cover 1300 that can be similar to back cover 1200 illustrated in FIG. 12. As shown in FIG. 13 opaque isolation regions 1310 similar to those described in FIGS. 12A-12D can be formed in both a top surface 1315 and a back surface 1320 of back cover 1300. Back cover 1300 is similar to back cover 1200 illustrated in FIGS. 12A-12D, however in this embodiment the back surface of back cover is not removed and instead one or more channels are formed in both top surface 1315 and back surface 1320 to optically isolate emitter regions from detector regions. For example, in region 1325 one opaque isolation region 1310 is formed in top surface 1315 and one opaque isolation region 1310 is formed in back surface 1320. A depth of each opaque isolation region 1310 is sufficient so light from an emitter cannot be detected by a detector. In some embodiments each opaque isolation region 1310 is the same depth, however in other embodiments the opaque isolation regions 1310 can have different depths. In region 1330 two opaque isolation regions 1310 are formed from top surface 1315 and one channel is formed from back surface 1320. In other embodiments a plurality of opaque isolation regions 1310 are formed in top surface 1315 and a plurality of channels are formed in back surface 1320. Any number and configuration of opaque isolation regions formed in top surface 1315 and back surfaces 1320 can be used and are within the scope of this disclosure. Further, as discussed in FIGS. 12A-12D, opaque isolation regions 1310 can be of any shape. In one embodiment opaque isolation regions 1310 are circular with the channel formed in top surface 1315 having a larger diameter than the channel formed in back surface 1320. However other configurations and geometries can be used and are within the scope of this disclosure.

Figure 14:
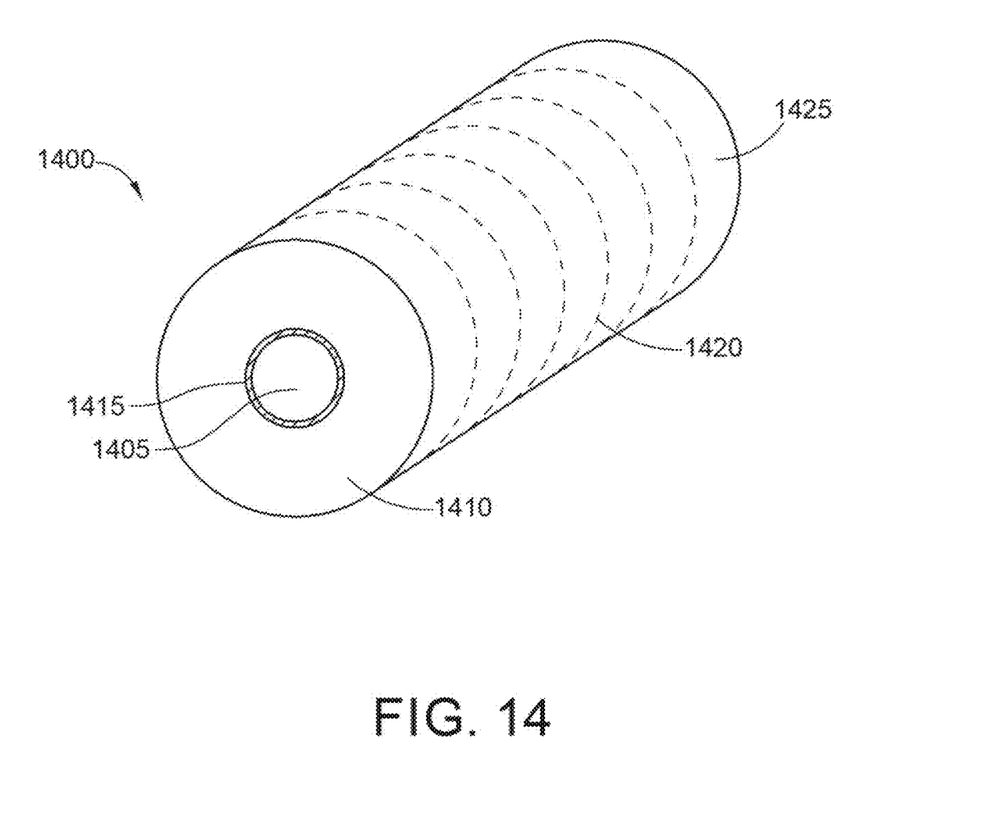
FIG. 14 illustrates a simplified perspective view of a dual window structure that can be used as a photosensor window in the portable electronic device illustrated in FIGS. 1A and 1B.

FIG. 14 illustrates a simplified perspective view of a dual window structure that can be used as a photosensor window in wearable electronic device 100 (see FIGS. 1A and 1B). As shown in FIG. 14, a cylinder 1400 composed of a first transparent region 1405 and a second transparent region 1410, separated by an opaque region 1415 can be formed, with portions thereof disposed within a back cover and used as windows for a photosensor. More specifically, a glass fiber can be used for first transparent region 1405 and the exterior surface can be metallized with the metallization functioning as opaque region 1415. A shell of transparent material can be formed over the opaque region 1415 forming second transparent region 1410. The process can be performed at an elevated temperature so when second transparent region 1410 cools it compresses against first transparent region 1405. The resulting cylinder 1400 can be cut along dashed lines 1420 into disks 1425 can be secured within openings within an opaque back cover, as discussed above with regard to FIGS. 6, 10 and 11. The resulting back cover can then have first and second transparent regions separated by an opaque region.

Although wearable electronic device 100 (see FIG. 1A) is described and illustrated as one particular electronic device, embodiments of the disclosure are suitable for use with a multiplicity of electronic devices. For example, any device that can come into contact with a user and used to collect physiological data from the user can be used with embodiments of the disclosure. In some embodiments electronic devices that receive or transmit audio, video or data signals can be used with embodiments of the disclosure. In some instances, embodiments of the disclosure are particularly well suited for use with portable electronic media devices because of their potentially small form factor. As used herein, an electronic media device includes any device with at least one electronic component that can be used to present human-perceivable media. Such devices can include, for example, portable music players (e.g., MP3 devices and Apple's iPod devices), portable video players (e.g., portable DVD players), cellular telephones (e.g., smart telephones such as Apple's iPhone devices), video cameras, digital still cameras, projection systems (e.g., holographic projection systems), gaming systems, PDAs, as well as tablet (e.g., Apple's iPad devices), laptop or other mobile computers. Some of these devices can be configured to provide audio, video or other data or sensory output.

For simplicity, various internal components, such as the control circuitry, graphics circuitry, bus, memory, storage device and other components of wearable electronic device 100 (see FIG. 1A) are not shown in the figures.

In the foregoing specification, embodiments of the disclosure have been described with reference to numerous specific details that can vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction. The specific details of particular embodiments can be combined in any suitable manner without departing from the spirit and scope of embodiments of the disclosure.

Additionally, spatially relative terms, such as "bottom or "top" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as a "bottom" surface can then be oriented "above" other elements or features. The device can be otherwise oriented (e.g., rotated 90 degrees or at other orientations) and the spatially relative descriptors used herein interpreted accordingly.

What is claimed is:

1. A wearable electronic device comprising:
a housing defining a top surface positioned opposite a bottom surface, the bottom surface defining a circular convex region that includes:
a central region aligned with at least one photoemitter;
a photodetector region aligned with at least one photodetector and defined around at least a portion of a perimeter of the central region;
a first opaque region separating the central region from the photodetector region, wherein the first opaque region is defined between an inner boundary encircling the central region and an outer boundary spaced apart from, and aligned with, the inner boundary; and
a second opaque region at least partially dividing the central region.

2. The wearable electronic device of claim 1 wherein the at least one photoemitter is positioned below the central region.

3. The wearable electronic device of claim 1 wherein the at least one photodetector is positioned below the photodetector region.

4. The wearable electronic device of claim 1 wherein the housing encloses a display.

5. The wearable electronic device of claim 4 wherein the display is a touch-sensitive display.

6. The wearable electronic device of claim 1 wherein the housing defines an external sidewall of the wearable electronic device.

7. The wearable electronic device of claim 6 further comprising a user input device positioned at the external sidewall.

8. The wearable electronic device of claim 1, wherein the outer boundary includes a first circular shape.

9. The wearable electronic device of claim 1, wherein the second opaque region extends from the inner boundary of the first opaque region into the central region.

10. A portable electronic device comprising:
a display;
an enclosure enclosing the display and defining a top surface positioned opposite a bottom surface, the bottom surface having a convex region that includes:
a central region aligned with at least one photoemitter;
a photodetector region aligned with at least one photodetector and defined around at least a portion of a perimeter of the central region;
a first opaque region separating the central region from the photodetector region, wherein the first opaque region is defined between an inner boundary encircling the central region and an outer boundary spaced apart from, and aligned with, the inner boundary; and
a second opaque region at least partially dividing the central region.

11. The portable electronic device of claim 10 wherein the at least one photoemitter is positioned below the central region.

12. The portable electronic device of claim 10 wherein the at least one photodetector is positioned below the photodetector region.

13. The portable electronic device of claim 10 wherein the display is a touch-sensitive display.

14. The portable electronic device of claim 10 further comprising a band attached to the enclosure.

15. The portable electronic device of claim 10 wherein the enclosure defines an external sidewall of the portable electronic device.

16. The portable electronic device of claim 15 further comprising a user input device positioned at the external sidewall.

17. A wearable electronic device comprising:
a housing defining a top surface positioned opposite a bottom surface, the bottom surface including a convex region defined within a circular perimeter, wherein the convex region includes:
a central region aligned with at least one photoemitter;
a photodetector region aligned with at least one photodetector and defined around at least a portion of a perimeter of the central region;
a first opaque region positioned between the central region and the photodetector region, wherein the first opaque region is defined between an inner boundary encircling the central region and an outer boundary spaced apart from, and aligned with, the inner boundary; and
a second opaque region at least partially dividing the central region.

18. The wearable electronic device of claim 17 wherein the at least one photoemitter is positioned below the central region.

19. The wearable electronic device of claim 17 wherein the at least one photodetector is positioned below the photodetector region.

20. The wearable electronic device of claim 17 wherein the housing encloses a display.

* * * * *